United States Patent
Damarati (10) Patent No.: US 9,248,311 B2
(45) Date of Patent: Feb. 2, 2016

(54) SYSTEM AND METHOD FOR MODIFYING A FLEXIBILITY OF A BRACHYTHEREAPY CATHETER

(75) Inventor: John Damarati, Marlborough, MA (US)

(73) Assignee: Hologic, Inc., Bedford, MA (US)

( * ) Notice: Subject to any disclaimer, the term of this patent is extended or adjusted under 35 U.S.C. 154(b) by 1194 days.

(21) Appl. No.: 12/369,236

(22) Filed: Feb. 11, 2009

(65) Prior Publication Data

US 2010/0204535 A1 Aug. 12, 2010

(51) Int. Cl.

| | |
|---|---|
| *A61N 5/00* | (2006.01) |
| *A61N 5/10* | (2006.01) |
| *A61M 25/00* | (2006.01) |
| *A61M 25/01* | (2006.01) |
| *A61M 37/00* | (2006.01) |
| A61M 25/04 | (2006.01) |
| A61M 25/10 | (2013.01) |

(52) U.S. Cl.
CPC ......... *A61N 5/1015* (2013.01); *A61M 25/0026* (2013.01); *A61M 25/0102* (2013.01); *A61M 37/0069* (2013.01); *A61M 25/0097* (2013.01); *A61M 25/04* (2013.01); *A61M 25/10* (2013.01); *A61N 2005/1018* (2013.01)

(58) Field of Classification Search
CPC ..................... A61M 25/0097; A61M 25/0102; A61M 2025/0681; A61M 2025/0059; A61M 2025/0063
USPC ............................ 600/1–8, 583; 128/897, 899
See application file for complete search history.

(56) References Cited

U.S. PATENT DOCUMENTS

| | | | |
|---|---|---|---|
| 3,324,847 | A | 6/1967 | Zoumboulis |
| 3,502,878 | A | 3/1970 | Stewart |
| 3,863,073 | A | 1/1975 | Wagner |
| 3,872,856 | A | 3/1975 | Clayton |
| 3,971,950 | A | 7/1976 | Evans et al. |
| 3,975,350 | A | 8/1976 | Hudgin et al. |
| 4,119,094 | A | 10/1978 | Micklus et al. |
| 4,160,906 | A | 7/1979 | Daniels et al. |
| 4,310,766 | A | 1/1982 | Finkenzeller et al. |

(Continued)

FOREIGN PATENT DOCUMENTS

| | | |
|---|---|---|
| DE | 25 39 553 | 3/1977 |
| EP | 0 340 881 | 10/1992 |

(Continued)

OTHER PUBLICATIONS

International Search Report and Written Opinion from related PCT Application No. PCT/US2010/023461 dated Jun. 1, 2010.

(Continued)

*Primary Examiner* — Charles A Marmor, II
*Assistant Examiner* — Shannon McBride (57) ABSTRACT

A flexible, multi-lumen brachytherapy device includes a plurality of loose lumens extend through a hub towards a single point of attachment at a distal rigid section. Because the lumens are attached at only a single distal location, the lumens are free to move axially and rotatably, thereby increasing the overall flexibility of the device to thereby decrease intermittent device movement while increasing patient comfort. A novel keyed stylet can be selectively inserted to increase the rigidity of the device as needed. The ability to dynamically modify the rigidity of the brachytherapy device provides a comprehensive brachytherapy solution that satisfies concerns of the patient, the surgeon and the radiologists.

17 Claims, 7 Drawing Sheets

(56) References Cited

U.S. PATENT DOCUMENTS

| | | |
|---|---|---|
| 4,350,169 A | 9/1982 | Dutcher et al. |
| 4,417,576 A | 11/1983 | Baran |
| 4,454,106 A | 6/1984 | Gansow et al. |
| 4,496,557 A | 1/1985 | Malen et al. |
| 4,559,641 A | 12/1985 | Caugant et al. |
| 4,571,241 A | 2/1986 | Christopher |
| 4,690,677 A | 9/1987 | Erb |
| 4,706,269 A | 11/1987 | Reina et al. |
| 4,706,652 A | 11/1987 | Horowitz |
| 4,744,099 A | 5/1988 | Huettenrauch et al. |
| 4,754,745 A | 7/1988 | Horowitz |
| 4,763,642 A | 8/1988 | Horowitz |
| 4,773,086 A | 9/1988 | Fujita et al. |
| 4,773,087 A | 9/1988 | Plewes |
| 4,819,258 A | 4/1989 | Kleinman et al. |
| 4,821,725 A | 4/1989 | Azam et al. |
| 4,821,727 A | 4/1989 | Levene et al. |
| 4,867,741 A | 9/1989 | Portnoy |
| 4,929,470 A | 5/1990 | Rittenhouse et al. |
| 4,969,174 A | 11/1990 | Scheid et al. |
| 4,989,227 A | 1/1991 | Tirelli et al. |
| 4,998,917 A | 3/1991 | Geiser et al. |
| 4,998,930 A | 3/1991 | Lundahl |
| 5,015,247 A | 5/1991 | Michaelson |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,059,166 A | 10/1991 | Fischell et al. |
| 5,078,142 A | 1/1992 | Siczek et al. |
| 5,084,001 A | 1/1992 | Van 't Hooft et al. |
| 5,084,015 A | 1/1992 | Moriuchi |
| 5,084,022 A | 1/1992 | Claude |
| 5,106,360 A | 4/1992 | Ishiwara et al. |
| 5,112,303 A | 5/1992 | Pudenz et al. |
| 5,152,747 A | 10/1992 | Olivier |
| 5,163,075 A | 11/1992 | Lubinsky et al. |
| 5,164,976 A | 11/1992 | Scheid et al. |
| 5,167,622 A | 12/1992 | Muto |
| 5,199,056 A | 3/1993 | Darrah |
| 5,199,939 A | 4/1993 | Dake et al. |
| 5,227,969 A | 7/1993 | Waggener et al. |
| 5,236,410 A | 8/1993 | Granov et al. |
| 5,240,011 A | 8/1993 | Assa |
| 5,259,847 A | 11/1993 | Trambert |
| 5,289,520 A | 2/1994 | Pellegrino et al. |
| 5,302,168 A | 4/1994 | Hess |
| 5,312,356 A | 5/1994 | Engelson et al. |
| 5,314,518 A | 5/1994 | Ito et al. |
| 5,336,178 A | 8/1994 | Kaplan et al. |
| 5,342,305 A | 8/1994 | Shonk |
| 5,359,637 A | 10/1994 | Webber |
| 5,365,562 A | 11/1994 | Toker |
| 5,381,504 A | 1/1995 | Novack et al. |
| 5,411,466 A | 5/1995 | Hess |
| 5,415,169 A | 5/1995 | Siczek et al. |
| 5,417,687 A | 5/1995 | Nardella et al. |
| 5,422,926 A | 6/1995 | Smith et al. |
| 5,426,685 A | 6/1995 | Pellegrino et al. |
| 5,428,658 A | 6/1995 | Oettinger et al. |
| 5,429,582 A | 7/1995 | Williams |
| 5,452,367 A | 9/1995 | Bick et al. |
| 5,484,384 A | 1/1996 | Fearnot |
| 5,503,613 A | 4/1996 | Weinberger |
| 5,506,877 A | 4/1996 | Niklason et al. |
| 5,520,646 A | 5/1996 | D'Andrea |
| 5,526,394 A | 6/1996 | Siczek et al. |
| 5,535,817 A | 7/1996 | Dunne |
| 5,539,797 A | 7/1996 | Heidsieck et al. |
| 5,553,111 A | 9/1996 | Moore et al. |
| 5,562,594 A | 10/1996 | Weeks |
| 5,566,221 A | 10/1996 | Smith et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzki et al. |
| 5,603,991 A | 2/1997 | Kupiecki et al. |
| 5,609,152 A | 3/1997 | Pellegrino et al. |
| 5,611,767 A | 3/1997 | Williams |
| 5,616,114 A | 4/1997 | Thornton et al. |
| 5,621,780 A | 4/1997 | Smith et al. |
| 5,624,395 A | 4/1997 | Mikhail et al. |
| 5,627,869 A | 5/1997 | Andrew et al. |
| 5,653,683 A | 8/1997 | D'Andrea |
| 5,657,362 A | 8/1997 | Giger et al. |
| 5,662,580 A | 9/1997 | Bradshaw et al. |
| 5,668,889 A | 9/1997 | Hara |
| 5,704,926 A | 1/1998 | Sutton |
| 5,706,327 A | 1/1998 | Adamkowski et al. |
| 5,719,952 A | 2/1998 | Rooks |
| 5,720,717 A | 2/1998 | D'Andrea |
| 5,724,400 A | 3/1998 | Swerdloff et al. |
| 5,735,264 A | 4/1998 | Siczek et al. |
| 5,741,253 A | 4/1998 | Michaelson |
| 5,759,173 A | 6/1998 | Preissman et al. |
| 5,769,086 A | 6/1998 | Ritchart et al. |
| 5,782,742 A | 7/1998 | Crocker et al. |
| 5,800,333 A | 9/1998 | Liprie |
| 5,803,895 A | 9/1998 | Kronholz et al. |
| 5,803,912 A | 9/1998 | Siczek et al. |
| 5,818,898 A | 10/1998 | Tsukamoto et al. |
| 5,820,594 A | 10/1998 | Fontirroche et al. |
| 5,820,717 A | 10/1998 | Siegenthaler |
| 5,828,722 A | 10/1998 | Ploetz et al. |
| 5,851,182 A | 12/1998 | Sahadevan |
| 5,863,284 A | 1/1999 | Klein |
| 5,863,285 A | 1/1999 | Coletti |
| 5,872,828 A | 2/1999 | Niklason et al. |
| 5,878,104 A | 3/1999 | Ploetz |
| 5,896,437 A | 4/1999 | Ploetz |
| 5,899,882 A | 5/1999 | Waksman et al. |
| 5,908,406 A | 6/1999 | Ostapchenko et al. |
| 5,913,813 A | 6/1999 | Williams et al. |
| 5,916,143 A | 6/1999 | Apple et al. |
| 5,919,473 A | 7/1999 | Elkhoury |
| 5,924,973 A | 7/1999 | Weinberger |
| 5,931,774 A | 8/1999 | Williams et al. |
| 5,935,098 A | 8/1999 | Blaisdell et al. |
| 5,986,662 A | 11/1999 | Argiro et al. |
| 5,993,972 A | 11/1999 | Reich et al. |
| 6,005,907 A | 12/1999 | Ploetz |
| 6,022,308 A | 2/2000 | Willaims |
| 6,022,325 A | 2/2000 | Siczek et al. |
| 6,033,357 A | 3/2000 | Ciezki et al. |
| 6,036,631 A | 3/2000 | McGrath et al. |
| 6,050,930 A | 4/2000 | Teirstein |
| 6,075,879 A | 6/2000 | Roehrig et al. |
| 6,083,148 A | 7/2000 | Williams |
| 6,086,970 A | 7/2000 | Ren |
| 6,091,841 A | 7/2000 | Rogers et al. |
| 6,093,142 A | 7/2000 | Ciamacco, Jr. |
| 6,095,966 A | 8/2000 | Chomenky et al. |
| 6,137,527 A | 10/2000 | Abdel-Malek et al. |
| 6,141,398 A | 10/2000 | He et al. |
| 6,143,013 A | 11/2000 | Samson et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,200,257 B1 | 3/2001 | Winkler |
| 6,216,540 B1 | 4/2001 | Nelson et al. |
| 6,217,565 B1 | 4/2001 | Cohen |
| 6,219,059 B1 | 4/2001 | Argiro |
| 6,233,473 B1 | 5/2001 | Shepherd et al. |
| 6,234,952 B1 | 5/2001 | Liprie |
| 6,243,441 B1 | 6/2001 | Zur |
| 6,251,059 B1 | 6/2001 | Apple et al. |
| 6,256,370 B1 | 7/2001 | Yavuz |
| 6,256,529 B1 | 7/2001 | Holupka et al. |
| 6,267,775 B1 | 7/2001 | Clerc et al. |
| 6,272,207 B1 | 8/2001 | Tang |
| 6,282,142 B1 | 8/2001 | Miyawaki |
| 6,289,235 B1 | 9/2001 | Webber et al. |
| 6,292,530 B1 | 9/2001 | Yavus et al. |
| 6,306,074 B1 | 10/2001 | Waksman et al. |

(56) References Cited

U.S. PATENT DOCUMENTS

| | | |
|---|---|---|
| 6,319,188 B1 | 11/2001 | Lovoi |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,378,137 B1 | 4/2002 | Hassan et al. |
| 6,390,967 B1 | 5/2002 | Forman et al. |
| 6,390,968 B1 | 5/2002 | Harmon |
| 6,390,992 B1 | 5/2002 | Morris et al. |
| 6,398,708 B1 | 6/2002 | Hastings et al. |
| 6,411,836 B1 | 6/2002 | Patel et al. |
| 6,413,203 B1 | 7/2002 | Sahatjian |
| 6,413,204 B1 | 7/2002 | Winkler et al. |
| 6,415,015 B2 | 7/2002 | Nicolas et al. |
| 6,416,457 B1 | 7/2002 | Urick et al. |
| 6,416,492 B1 | 7/2002 | Nielson |
| 6,442,288 B1 | 8/2002 | Haerer et al. |
| 6,458,069 B1 | 10/2002 | Tam et al. |
| 6,458,070 B1 | 10/2002 | Waksman et al. |
| 6,459,925 B1 | 10/2002 | Nields et al. |
| 6,482,142 B1 | 11/2002 | Winkler et al. |
| 6,501,819 B2 | 12/2002 | Unger et al. |
| 6,512,942 B1 | 1/2003 | Burdette et al. |
| 6,527,693 B2 | 3/2003 | Munro, III et al. |
| 6,540,655 B1 | 4/2003 | Chin et al. |
| 6,556,655 B1 | 4/2003 | Chichereau et al. |
| 6,558,390 B2 | 5/2003 | Cragg |
| 6,579,221 B1 | 6/2003 | Peterson |
| 6,597,762 B1 | 7/2003 | Ferrant et al. |
| 6,605,030 B2 | 8/2003 | Weinberger |
| 6,607,477 B1 | 8/2003 | Longton et al. |
| 6,610,013 B1 | 8/2003 | Fenster et al. |
| 6,611,575 B1 | 8/2003 | Alyassin et al. |
| 6,615,070 B2 | 9/2003 | Lee |
| 6,616,629 B1 | 9/2003 | Verin et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,673,006 B2 | 1/2004 | Winkler |
| 6,685,618 B2 | 2/2004 | Tam et al. |
| 6,706,014 B2 | 3/2004 | Banik et al. |
| 6,723,052 B2 | 4/2004 | Mills |
| 6,744,848 B2 | 6/2004 | Stanton et al. |
| 6,746,392 B2 | 6/2004 | Stiger et al. |
| 6,748,044 B2 | 6/2004 | Sabol et al. |
| 6,749,555 B1 | 6/2004 | Winkler et al. |
| 6,749,595 B1 | 6/2004 | Murphy |
| 6,751,285 B2 | 6/2004 | Eberhard et al. |
| 6,752,752 B2 | 6/2004 | Geitz |
| 6,758,824 B1 | 7/2004 | Miller et al. |
| 6,770,058 B1 | 8/2004 | Liprie |
| 6,813,334 B2 | 11/2004 | Koppe et al. |
| 6,882,700 B2 | 4/2005 | Wang et al. |
| 6,885,724 B2 | 4/2005 | Li et al. |
| 6,912,319 B1 | 6/2005 | Barnes et al. |
| 6,913,600 B2 | 7/2005 | Valley et al. |
| 6,923,754 B2 | 8/2005 | Lubock |
| 6,940,943 B2 | 9/2005 | Claus et al. |
| 6,955,641 B2 | 10/2005 | Lubock |
| 6,970,531 B2 | 11/2005 | Eberhard et al. |
| 6,978,040 B2 | 12/2005 | Berestov |
| 6,983,754 B1 | 1/2006 | Anderson et al. |
| 6,987,831 B2 | 1/2006 | Ning |
| 6,999,554 B2 | 2/2006 | Mertelmeier |
| 7,098,463 B2 | 8/2006 | Adamovics |
| 7,107,089 B2 | 9/2006 | Lee |
| 7,110,490 B2 | 9/2006 | Eberhard et al. |
| 7,110,502 B2 | 9/2006 | Tsuji |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,171,255 B2 | 1/2007 | Holupka et al. |
| 7,201,715 B2 | 4/2007 | Burdette et al. |
| 7,214,178 B2 | 5/2007 | Lubock |
| 7,245,694 B2 | 7/2007 | Jing et al. |
| 7,315,607 B2 | 1/2008 | Ramsauer |
| 7,319,735 B2 | 1/2008 | Defreitas |
| 7,322,929 B2 | 1/2008 | Lovoi |
| 7,323,692 B2 | 1/2008 | Rowlands et al. |
| 7,404,791 B2 | 7/2008 | Linares et al. |
| 7,407,476 B2 | 8/2008 | Lubock et al. |
| 7,413,539 B2 | 8/2008 | Lubock et al. |
| 7,430,272 B2 | 9/2008 | Jing et al. |
| 7,443,949 B2 | 10/2008 | Defreitas et al. |
| 7,465,268 B2 | 12/2008 | Lubock et al. |
| 7,476,235 B2 | 1/2009 | Diederich et al. |
| 7,497,819 B2 | 3/2009 | White et al. |
| 7,497,820 B2 | 3/2009 | White et al. |
| 7,513,861 B2 | 4/2009 | Klein et al. |
| 7,517,310 B2 | 4/2009 | Lubock et al. |
| 7,609,806 B2 | 10/2009 | Defreitas et al. |
| 7,630,533 B2 | 12/2009 | Ruth et al. |
| 7,662,082 B2 | 2/2010 | White et al. |
| 7,697,660 B2 | 4/2010 | Ning |
| 7,783,006 B2 | 8/2010 | Stewart et al. |
| 7,792,245 B2 | 9/2010 | Hitzke et al. |
| 7,869,563 B2 | 1/2011 | Defreitas et al. |
| 7,885,382 B2 | 2/2011 | Stewart et al. |
| 7,887,476 B2 | 2/2011 | Hermann et al. |
| 8,075,469 B2 | 12/2011 | Lubock et al. |
| 8,079,946 B2 | 12/2011 | Lubock et al. |
| 8,137,256 B2 | 3/2012 | Cutrer et al. |
| 8,192,344 B2 | 6/2012 | Lubock et al. |
| 8,277,370 B2 | 10/2012 | Quick |
| 8,287,442 B2 | 10/2012 | Quick |
| 8,565,374 B2 | 10/2013 | Defreitas et al. |
| 2001/0016725 A1 | 8/2001 | Valley et al. |
| 2001/0038681 A1 | 11/2001 | Stanton et al. |
| 2001/0038861 A1 | 11/2001 | Hsu et al. |
| 2001/0049464 A1 | 12/2001 | Ganz |
| 2001/0051669 A1 | 12/2001 | McGhee |
| 2002/0012450 A1 | 1/2002 | Tsujii |
| 2002/0026090 A1 | 2/2002 | Kaplan et al. |
| 2002/0045893 A1 | 4/2002 | Lane et al. |
| 2002/0050986 A1 | 5/2002 | Inoue et al. |
| 2002/0055666 A1 | 5/2002 | Hunter et al. |
| 2002/0075997 A1 | 6/2002 | Unger et al. |
| 2002/0095114 A1 | 7/2002 | Palasis |
| 2002/0156342 A1 | 10/2002 | Burton et al. |
| 2002/0177804 A1 | 11/2002 | Saab |
| 2003/0018272 A1 | 1/2003 | Treado et al. |
| 2003/0073895 A1 | 4/2003 | Nields et al. |
| 2003/0095624 A1 | 5/2003 | Eberhard |
| 2003/0144570 A1 | 7/2003 | Hunter et al. |
| 2003/0153803 A1 | 8/2003 | Harmon |
| 2003/0194050 A1 | 10/2003 | Eberhard |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0039437 A1 | 2/2004 | Sparer et al. |
| 2004/0054366 A1 | 3/2004 | Davison et al. |
| 2004/0066884 A1 | 4/2004 | Hermann Claus et al. |
| 2004/0066904 A1 | 4/2004 | Eberhard et al. |
| 2004/0087827 A1 | 5/2004 | Lubock |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0116767 A1 | 6/2004 | Lebovic et al. |
| 2004/0147800 A1 | 7/2004 | Barber et al. |
| 2004/0171986 A1 | 9/2004 | Tremaglio, Jr. et al. |
| 2004/0215048 A1 | 10/2004 | Lubock |
| 2004/0260142 A1 | 12/2004 | Lovoi |
| 2004/0267157 A1 | 12/2004 | Miller et al. |
| 2005/0016771 A1 | 1/2005 | Mayes et al. |
| 2005/0049521 A1 | 3/2005 | Miller et al. |
| 2005/0061771 A1 | 3/2005 | Murphy |
| 2005/0063509 A1 | 3/2005 | DeFreitas et al. |
| 2005/0078797 A1 | 4/2005 | Danielsson et al. |
| 2005/0080313 A1 | 4/2005 | Stewart et al. |
| 2005/0101823 A1 | 5/2005 | Linares et al. |
| 2005/0105679 A1 | 5/2005 | Wu et al. |
| 2005/0113681 A1 | 5/2005 | DeFreitas et al. |

(56) References Cited

U.S. PATENT DOCUMENTS

| | | |
|---|---|---|
| 2005/0113715 A1 | 5/2005 | Schwindt et al. |
| 2005/0124843 A1 | 6/2005 | Singh |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0182286 A1 | 8/2005 | Lubock |
| 2005/0226375 A1 | 10/2005 | Eberhard et al. |
| 2005/0240073 A1 | 10/2005 | Apffelstaedt et al. |
| 2005/0240074 A1 | 10/2005 | Lubock |
| 2005/0267320 A1 | 12/2005 | Barber et al. |
| 2005/0277577 A1 | 12/2005 | Hunter et al. |
| 2006/0020156 A1 | 1/2006 | Shukla |
| 2006/0020256 A1 | 1/2006 | Bell et al. |
| 2006/0030784 A1 | 2/2006 | Miller et al. |
| 2006/0074288 A1 | 4/2006 | Kelly |
| 2006/0098855 A1 | 5/2006 | Gkanatsios |
| 2006/0100475 A1 | 5/2006 | White et al. |
| 2006/0116546 A1 | 6/2006 | Eng |
| 2006/0129062 A1 | 6/2006 | Nicoson et al. |
| 2006/0136051 A1 | 6/2006 | Furst et al. |
| 2006/0155209 A1 | 7/2006 | Miller et al. |
| 2006/0167416 A1 | 7/2006 | Mathis et al. |
| 2006/0173233 A1 | 8/2006 | Lovoi |
| 2006/0173235 A1 | 8/2006 | Lim et al. |
| 2006/0205992 A1 | 9/2006 | Lubock et al. |
| 2006/0291618 A1 | 12/2006 | Eberhard et al. |
| 2007/0005003 A1 | 1/2007 | Patterson et al. |
| 2007/0030949 A1 | 2/2007 | Jing et al. |
| 2007/0036265 A1 | 2/2007 | Jing et al. |
| 2007/0055144 A1 | 3/2007 | Neustadter et al. |
| 2007/0076844 A1 | 4/2007 | Defreitas et al. |
| 2007/0106108 A1 | 5/2007 | Hermann et al. |
| 2007/0142694 A1 | 6/2007 | Cutrer et al. |
| 2007/0167665 A1 | 7/2007 | Hermann et al. |
| 2007/0167666 A1 | 7/2007 | Lubock et al. |
| 2007/0191667 A1 | 8/2007 | Lubock et al. |
| 2007/0223651 A1 | 9/2007 | Wagenaar et al. |
| 2007/0225600 A1 | 9/2007 | Weibrecht |
| 2007/0242800 A1 | 10/2007 | Jing |
| 2007/0270627 A1 | 11/2007 | Cutrer et al. |
| 2008/0009659 A1 | 1/2008 | Smith et al. |
| 2008/0019581 A1 | 1/2008 | Gkanatsios |
| 2008/0045833 A1 | 2/2008 | Defreitas |
| 2008/0057298 A1 | 3/2008 | Finley |
| 2008/0064915 A1 | 3/2008 | Lubock |
| 2008/0086083 A1 | 4/2008 | Towler |
| 2008/0091055 A1 | 4/2008 | Nguyen et al. |
| 2008/0101537 A1 | 5/2008 | Sendai |
| 2008/0112534 A1 | 5/2008 | DeFreitas et al. |
| 2008/0130979 A1 | 6/2008 | Ren |
| 2008/0177127 A1 | 7/2008 | Allan et al. |
| 2008/0188705 A1 | 8/2008 | Lubock et al. |
| 2008/0221384 A1 | 9/2008 | Chi Sing et al. |
| 2008/0221444 A1 | 9/2008 | Ritchie et al. |
| 2008/0228023 A1 | 9/2008 | Jones et al. |
| 2008/0228024 A1 | 9/2008 | Jones et al. |
| 2008/0228025 A1 | 9/2008 | Quick |
| 2008/0228150 A1 | 9/2008 | Jones et al. |
| 2008/0281142 A1 | 11/2008 | Lubock et al. |
| 2008/0281143 A1 | 11/2008 | Lubock et al. |
| 2008/0287801 A1 | 11/2008 | Magnin et al. |
| 2009/0003519 A1 | 1/2009 | Defreitas |
| 2009/0010384 A1 | 1/2009 | Jing |
| 2009/0030259 A1 | 1/2009 | Quick |
| 2009/0080594 A1 | 3/2009 | Brooks |
| 2009/0080602 A1 | 3/2009 | Brooks |
| 2009/0093821 A1 | 4/2009 | Edmundson |
| 2009/0124845 A1 | 5/2009 | Lubock et al. |
| 2009/0135997 A1 | 5/2009 | Defreitas |
| 2009/0156880 A1 | 6/2009 | Allan et al. |
| 2009/0156882 A1 * | 6/2009 | Chi Sing et al. ............... 600/7 |
| 2009/0171157 A1 | 7/2009 | Diederich et al. |
| 2009/0188098 A1 | 7/2009 | Acosta et al. |
| 2009/0198095 A1 | 8/2009 | Acosta et al. |
| 2009/0213987 A1 | 8/2009 | Stein et al. |
| 2009/0268865 A1 | 10/2009 | Ren |
| 2009/0296882 A1 | 12/2009 | Gkanatsios |
| 2009/0304147 A1 | 12/2009 | Jing et al. |
| 2010/0048977 A1 | 2/2010 | Sing et al. |
| 2010/0054400 A1 | 3/2010 | Ren |
| 2010/0086188 A1 | 4/2010 | Ruth |
| 2010/0150306 A1 | 6/2010 | Defreitas et al. |
| 2010/0195882 A1 | 8/2010 | Ren |
| 2010/0204534 A1 | 8/2010 | Damarati |
| 2010/0226475 A1 | 9/2010 | Smith |
| 2010/0286465 A1 | 11/2010 | Benson |
| 2010/0290585 A1 | 11/2010 | Eliasson |
| 2011/0069809 A1 | 3/2011 | Defreitas et al. |
| 2012/0071705 A1 | 3/2012 | Lubock et al. |
| 2012/0178983 A1 | 7/2012 | Benson |

FOREIGN PATENT DOCUMENTS

| | | |
|---|---|---|
| EP | 0536440 | 4/1993 |
| EP | 0642766 | 3/1995 |
| EP | 0693293 | 1/1996 |
| EP | 0719571 | 7/1996 |
| EP | 775467 | 5/1997 |
| EP | 0853957 | 7/1998 |
| EP | 0 867 200 | 9/1998 |
| EP | 0982001 | 3/2000 |
| EP | 1051990 | 11/2000 |
| EP | 1070514 | 1/2001 |
| EP | 1402922 | 3/2004 |
| EP | 1428473 | 6/2004 |
| EP | 1541188 | 6/2005 |
| EP | 1618924 | 1/2006 |
| EP | 1759637 | 3/2007 |
| JP | 10137250 | 5/1998 |
| JP | 2001120561 | 5/2001 |
| RU | 2177350 | 12/2001 |
| WO | WO 90/05485 | 5/1990 |
| WO | WO 92/10932 | 7/1992 |
| WO | WO 93/09724 | 5/1993 |
| WO | WO 9520241 | 7/1995 |
| WO | WO 9712540 | 4/1997 |
| WO | WO 97/19723 | 6/1997 |
| WO | WO 97/45053 | 12/1997 |
| WO | WO 98/16903 | 4/1998 |
| WO | WO 9815315 | 4/1998 |
| WO | WO 99/11325 | 3/1999 |
| WO | WO 99/33515 | 7/1999 |
| WO | WO 9934869 | 7/1999 |
| WO | WO 99/42163 | 9/1999 |
| WO | WO 01/14011 | 7/2000 |
| WO | WO 00/51484 | 9/2000 |
| WO | WO 01/43826 | 6/2001 |
| WO | WO 01/58346 | 8/2001 |
| WO | WO 02/09599 | 2/2002 |
| WO | WO 02/069862 | 9/2002 |
| WO | WO 03/020114 | 3/2003 |
| WO | WO 2004/043531 | 5/2004 |
| WO | WO 2004/043535 | 5/2004 |
| WO | WO 2005/037363 | 4/2005 |
| WO | WO 2005039655 | 5/2005 |
| WO | WO 2005039665 | 5/2005 |
| WO | WO 2005/051197 | 6/2005 |
| WO | WO 2005/067442 | 7/2005 |
| WO | WO 2005110230 | 11/2005 |
| WO | WO 2005112767 | 12/2005 |
| WO | WO 2006/055830 | 5/2006 |
| WO | WO 2006/058160 | 6/2006 |
| WO | WO 2007/027831 | 3/2007 |
| WO | WO 2007/143560 | 12/2007 |
| WO | WO 2008/067557 | 6/2008 |
| WO | WO 2009/079170 | 6/2009 |

OTHER PUBLICATIONS

International Search Report and Written Opinion from related PCT Application No. PCT/US2010/023454 dated May 7, 2010.
International Search Report and Written Opinion from related PCT Application No. PCT/US2010/033370 dated Jul. 30, 2010.

(56) References Cited

OTHER PUBLICATIONS

Nath, Ph.D. et al., Development of an 241 Am Applicator for Intracavitary Irradiation of Gynecologic Cancers, I.J. Radiation Oncology Biol. Phys., May 1988, vol. 14, p. 969-978.
Ashpole, et al., "A New Technique of Brachytherapy for Malignant Gliomas with Caesium-137: A New Method Utilizing a Remote Afterloading System," Clinical Oncology, p. 333-7.
International Search Report and Written Opinion from related PCT Application No. PCT/US2010/033373 dated Aug. 9, 2010.
"Essentials for life: Senographe Essential Full-Field Digital Mammography system", GE Health-care Brochure, MM-0132-05.06-EN-US, 2006, 12 pgs.
"Filtered Back Projection," (NYGREN) published May 8, 2007; URL:http://web.archive.org/web/19991010131715/http://www.owlnet.rice.edu/-.about.e1ec539/Projects97/cult/node2.html, 2 pgs.
"Lorad Selenia" Document B-BI-SEO US/Intl (May 2006), copyright Hologic 2006, 12 pgs.
"Variable shield for radiation-therapy sourcewire and centering catheter", Research disclosure, Mason Publications, Hampshire, GB, vol. 438, No. 48, Oct. 2000, XP007126916, 1 page.
Abstracts of the 11th International Conference on Brain tumor Research and Therapy Oct. 31-Nov. 3, 1995, Silverado Country Club and Resort, Napa, California, Journal of Neuro-Oncology 28, p. 72, 1996, 2 pages all together.
Akagi, Y, et al.,"Optimum Fractionation for High-Dose-Rate Endoesophageal Brachytherapy Following External Irradiation of Early State Esophageal Cancer", Int. J. Radiation Oncology Biol. Phys., vol. 43, 1999, pp. 525-530, Elsevier Science, Inc.
Astrahan, Melvin A., PhD et al., "Optimization of Mammosite therapy", Int. J. Radiation Oncology Biol. Phys, vol. 58, No. 1, pp. 220-232, 2004.
Bowsher. W. G., et al., "Update on Urology-Prostate Cancer. 4-Treatment of Local Disease". European Journal of Surgical Oncology. 1995 pp. 679-682. vol. 21. No. 6.
Chan, Heang-Ping et al., "ROC study of the effect of stereoscopic imaging on assessment of breast lesions", Medica Physics, vol. 32, No. 4, Apr. 2005, 7 pgs.
Cole, Elodia, et al., "The Effects of Gray Scale Image Processing on Digital Mammography Interpretation Performance", Academic Radiology, vol. 12, No. 5, pp. 585-595, May 2005.
Cuttino, L. W., et al.,"CT-Guided Multi-Catheter Insertion Technique for Partial Breast Brachytherapy: Reliable Target Coverage and Dose Homogeneity", Brachy1herapy 4, 2005, pp. 10-17, Elsevier.
Das, R. K., et al., "3D-CT-Based High-Dose-Rate Breast Brachytherapy Implants: Treatment Planning and Quality Assurance", Int. J. Radiation Oncology Biol. Phys. 2004, pp. 1224-1228, vol. 59, No. 4, Elsevier Inc.
Debicki, M. P., et al., "Localized Current Field Hyperthermia in Carcinoma of the Cervix: 3-D Computer Simulation of SAR Distribution". International Journal of Hyperthermia. 1999. pp. 427-440. vol. 15. No. 5.
Demanes, D. J . et al., "The Use and Advantages of a Multichannel Vaginal Cylinder in High-Dose-Rate Brachytherapy". Int. J. Radiation Oncology Biol. Phys. (1999). pp. 211-219. vol. 44. No. 1. Elsevier Science Inc.
Dempsey, J. F. et al., "Dosimetric Properties of a Novel Brachytherapy Balloon Applicator for the Treatment of Malignant Brain-Tumor Resection-Cavity Margins", Int. J. Radiation Oncology Biol. Phys., May 1998, pp. 421-429, vol. 42. No. 2. Elsevier.
Devic et al., "Advantages of Inflatable Multichannel Endorectal Applicator in the Neo-Adjuvant Treatment of Patients with Locally Advanced Rectal Cancer with HOR Brachytherapy", Journal of Applied Clinical Medical Physics, Spring 2005, pp. 44-49, vol. 6, No. 2.
Digital Clinical Reports, Tomosynthesis, GE Brochure 98-5493, Nov. 1998, 8 pgs.
Edmundson,Gregory K. et al., "Dosimetric Characteristics of the Mammosite RTS, a New Breast Brachytherapy Applicator", Int. J. Radiation Oncology Biol. Phys., vol. 52, No. 4, pp. 1132-1139, 2002.

Federica Pediconi et al., "Color-coded automated signal intensity-curve for detection and characterization of breast lesions: Preliminary evaluation of a new software for MR-based breast imaging", International Congress Series 1281 (2005) 1081-1086.
Fowler, J. E., "Brief Summary of Radiobiological Principles in Fractionated Radiotherapy", Seminars in Radiation Oncology, Jan. 1992, pp. 16-21, vol. 2, No. 1, W. B. Saunders Company.
Friedman, M, et al., "A New Technic for the Radium Treatment of Carcinoma of the Bladder", Presented at the Thirty-fourth Annual Meeting of the Radiological Society of North America, Dec. 5-10, 1948, pp. 342-362.
Friedman, M, et al., "Irradiation of Carcinoma of the Bladder by a Central Intracavitary Radium or Cobalt 60 Source (The Walter Reed Technique)", Presented at the Annual Meeting of the American Radium Society, 1955, pp. 6-31.
Garipagaoglu, M. et al., "Geometric and Dosimetric Variations of ICRU Bladder and Rectum Reference Points in Vaginal Cuff Brachytherapy Using Ovoids", Int. J. Radiation Oncology Biol. Phys. 2004, pp. 1607-1615. Elsevier Inc.
Gaspar, L. E., et al., "Esophageal Brachytherapy", Principles and Practice of Brachytherapy, 1997, pp. 305-321, Futrua Publishing Company, Inc., Armouk, New York.
Glasgow, G. P., et al. "Remote Afterloading Technology", AAPM Report No. 41, 1993, pp. i-vi and 1-107, American Institute of Physics, Inc., 116 pgs.
Gutin, P.H. et al., "A coaxial catheter system for afterloading radioactive sources for the interstitial irradiation of brain tumors", J. Neurosur, vol. 56, pp. 734-735, 1982.
Hall, J. W., et al., "Histologic Changes in Squamous-Cell Carcinoma of the Mouth and Oropharynx Produced by Fractionated External Roentgen Irradiation", Radiological Society of North America, 1948, pp. 318-350, Mar. 3, 1950.
Harada, T, et al.,"Transcystoscopic Intracavitary irradiation for Carcinoma of the Bladder: Technique and Preliminary Clinical Results", The Journal of Urology, Oct. 1987, pp. 771-774, vol. 138, No. 4, The Williams & Wilkins Co.
Harper, Paul V., "Some Therapeutic Applications of Radioisotopes", Journal of the Mississippi State Medical Association, Oct. 1966, vol. VII, pp. 526-533.
Hewitt, C. B., et al., "Intracavitary Radiation in the Treatment of Bladder Tumors", The Journal of Urology, vol. 107, Apr. 1972, pp. 603-606, The Williams & Wilkins Co.
Hewitt, C. B., et al., "Update on Intracavitary Radiation in the Treatment of Bladder Tumors", The Journal of Urology; Official Journal of the American Urological Association, Inc., 1981, pp. 323-325, vol. 126 September, The Williams & Wilkins Co.
Hieshima,G. B., et al. "A Detachable Balloon for Therapeutic Transcatheter Occlusions 1", Technical Notes, Jan. 1981, pp. 227-228, vol. 138.
Hine, G. J., et al., "Isodose Measurements of Linear Radium Sources in Air and Water by Means of an Automatic Isodose Recorder", The American Journal of Roentgenology and Radium Therapy, 1950, pp. 989-998, vol. 64, No. 6, The Societies.
Hoshino, T., "Brain Tumor Research Center", Abstracts of the 11th Conference on Brain Tumor Research and Therapy, Journal of Neuro-Oncology 28, 1996, pp. 31-113.
Johannesen, T.B. et al, "Intracavity Fractioned Balloon Brachytherapy in Glioblastoma", Acta Neurochir (Wien) (1999) 141: 127-133.
Kaufman, N., "Remote Afterloading Intraluminal Brachytherapy in the Treatment of Rectal, Rectosigmoid, and Anal Cancer: A Feasibility Study", International Journal of Radiation Oncology, Biology, Physics, Sep. 1989, pp. 663-668, vol. 17, Issue 3, Pergamon Press pic.
Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.
Kolotas., C. et al., "CT Guided Interstitial High Dose Rate Brachytherapy for Recurrent Malignant Gliomas". The British Journal of Radiology. 72. (1999), pp. 805-808.
Kuettel, M. R. et al.. "Treatment of Female Urethral Carcinoma in Medically Inoperable Patients Using External Beam Irradiation and (56) References Cited

OTHER PUBLICATIONS

High Dose Rate Intracavitary Brachytherapy", The Journal of Urology. May 1997, pp. 1669-1671, vol. 157, The American Urological Association, Inc.
Lewis, J, et al., "Intracranial Brachytherapy Using a High Dose Rate Microselectron", Northern Centre for Cancer Treatment, Dept. of Neurosciences, Regional Medical Physics Department, Newcastle General Hospital, Newcastle Upon Tyne, UK, Radiation and Oncology, vol. 39, Supplement 1, May 1996, pp. 45-45, 1 page, p. 179.
Low-Beer, B. V. A., "Radioisotope Therapy", "The Clinical Use of Radioactive Isotopes", 1950, pp. 284-349, Charles C. Thomas, Publisher, Springfield, Illinois, U.S.A., See pp. 343-349.
Low-Beer, B. V. A., "The Therapeutic Use of Radioactive Isotopes", "Practical Therapeutics", Dec. 1954, pp. 69-87, vol. X, No. 6.
Mammographic Accreditation Phantom, http://www.cirsinc.com/pdfs/015cp.pdf, (2006), 2 pgs.
Marshall V. F., et al., "Current Clinical Problems Regarding Bladder Tumors", Symposium on Bladder Tumors, 1956, pp. 543-550, 9/3/May-Jun., J.B. Lippincott Co, Etc.
Micheletti, E., et al., "High-Dose-Rate Brachytherapy for Poor-Prognosis, High-Grade Glioma: (Phase II) Preliminary Results", Tumori, 1996, pp. 339-344.
Muller, J. H., "Radiotherapy of Bladder Cancer by Means of Rubber Balloons Filled In Situ With solutions of a Radioactive Isotope (Co60)", Cancer, A Journal of the American Cancer Society, Jul.-Aug. 1955, pp. 1035-1043, vol. 8, No. 4, J.B. Lippincott Company, Philadelphia.
Nag, S, "Modern Techniques of Radiation Therapy for Endometrial Cancer", Clinical Obstetrics and Gynecology, Sep. 1996, pp. 728-744, vol. 39, No. 3, Lippincott-Raven Publishers.
Nag, S., et al., "Perineal Template Interstitial Barchytherapy Salvage for Recurrent Endometrial Adenocarcinoma Metastatic to the Vagina", Necologic Oncology 66, 1997, pp. 16-19, Article No. G0974722, Academic Press.
Nag, S., et al., "Remote Controlled High Dose Rate Brachytherapy", Critical Reviews in Oncology/Hematology 22, 1996, pp. 127-150, Elsevier Science Ireland Ltd.
Nag, S., et al., "The Future of High Dose Rate Brachytherapy", High Dose Rate Brachytherapy: A Textbook, 1994, pp. 447-453, Futura Publishing Company, Inc. , Armonk, New York 10504.
Pernot, M., "Combined Surgery and Brachytherapy in the Treatment of Some Cancers of the Bladder (Partial Cystectomy and Interstitial Iridium—192)", Radiotherapy & Oncology, 1996, pp. 115-120, Elsevier Science Ireland Ltd.
Rotman, M., et al., "The Intracavitary Applicator in Relation to Complications of Pelvic Radiation—The Ernst System", Int. J. Radiation Oncology Biol. Phys., 1978, pp. 951-956, vol. 4, Pergamon Press Inc.
Russel, A.H., et al, "Intracavitary Irradiation for Carcinoma of the Urinary Bladder: Rationale, Technique, and Preliminary Results", Int. J. Radiation Oncology. Phys., 1984, pp. 215-219, vol. 10, Pergamon Press Ltd.
Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.
Slevin. N. J. et al., "Intracavitary Radiotherapy Boosting for Nasopharynx Cancer", The British Journal of Radiology, 70, Apr. 1997, pp. 412-414.
Smith, A., "Fundamentals of Breast Tomosynthesis", White Paper, Hologic Inc., WP-00007, Jun. 2008, 8 pgs.
Sneed. P. K. et al., "Interstitial Brachytherapy Procedures for Brain Tumors", Seminars in Surgical Oncology 1997; 13: 157-166. Wiley-Liss. Inc.
Stubbs, J.B., et al.,"Preclinical Evaluation of a Novel Device for Delivering Brachytherapy to the Margins of Resected Brain Tumor Cavities", J. Neurosurg 96, Feb. 2002, pp. 335-343, vol. 96.
Sylvester, J., et al., "Interstitial Implantation Techniques in Prostate Cancer", Journal of Surgical Oncology 1997; 66: 65-75. Wiley-Liss. Inc.
Symon et al., "Individual Fraction Optimization vs. First Fraction Optimization for Multichannel Applicator Vaginal Cuff High-Dose-Rate Brachytherapy", pp. 211-215, Brachytherapy 5 (2006), Elsevier.
Tan, L. T. et al., "Radical Radiotherapy for Carcinoma of the Uterine Cervix Using External Beam Radiotherapy and a Single Line Source Brachytherapy Technique: The Clatterbridge Technique", The British Journal of Radiology, 70, Dec. 1997, pp. 1252-1258.
Tanderup et al. "Multi-Channel Intracavitary Vaginal Brachytherapy Using Three-Dimensional Optimization of Source Geometry", Radiation & Oncology Journal of the European Society for Therapeutic Radiology and Oncology, 2004, pp. 81-85, Radiotherapy and Oncology 70 (2004), Elsevier Ireland Ltd.
Vicini, F. A., et al, "Dose-Volume Analysis for Quality Assurance of Interstitial Brachytherapy for Breast Cancer", Int. J. Radiation Oncology Biol. Phys., vol. 45, 1999, pp. 803-810, Elsevier Science Inc.
Voung, T, et al., "High-Dose-Rate Endorectal Brachytherapy in the Treatment of Loacally Advanced Rectal Carcinoma: Technical Aspects", Brachytherapy 4, 2005, pp. 230-235, Elsevier.
Walton, R. J., "Therapeutic Uses of Radioactive Isotopes in the Royal Cancer Hospital", The British Journal of Radiology, 1950, pp. 559-599, William Heinemann, Publisher.
Walton, R. J., et al., Radioactive Solution (24Na and 82 Br) in the Treatment of Carcinoma of the Bladder:, British Medical Bulletin, 1952, pp. 158-165, Medical Dept., The British Council.
Wang, C. C., "Carcinoma of the Nasopharynx", Radiation Therapy of Head and Neck Neoplasms, 1997, pp. 257-280, Chapter 10, Wiley-Liss, Inc.
Wheeler, F.W. et al. (2006), "Micro-Calcification Detection in Digital Tomosynthesis Mammography", Proceedings of SPIE, Conf-Physics of Semiconductor Devices, Dec. 11, 2001 to Dec. 15, 2001, Delhi, SPIE, US, vol. 6144, Feb. 13, 2006, 12 pgs.
Wolf, C. D., et al., "A Unique Nasopharynx Brachytherapy Technique", Official Journal of the American Association of Medical Dosimetrists, 1990, pp. 133-136, vol. 15, Issue No. 3., Pergamon Press.
Wu, Tao et al., "Tomographic mammography using a limited number of low-dose cone-beam images", Medical Physics, AIP, Melville, NY, vol. 30, No. 3, Mar. 1, 2003, pp. 365-380.
"DuPont Teflon PFA HP Plus", XP007904995:retrieved from the internet: URL: http://www2.dupont.com/Teflon_Industrial/en_US/assets/downloads/ h88800.pdf; retrieved on Jun. 19, 2008, by Authorized Officer in International Application PCT/US2008/003364, 4 pgs.
Xu, Z., et al., "Calculation of Dose Distribution Near an Innovative Concentric Balloon Catheter for Endovascular Brachytherapy", Cardiovascular Radiation Medicine 2, 2000, pp. 26-31, Elsevier Science Inc.
Yin, W., "Brachtherapy of Carcinoma of the Esophagus in China, 1970-1974 and 1982-1984", Brachytherapy HOR and LOR, May 4-6, 1989, pp. 52-56.

* cited by examiner

SYSTEM AND METHOD FOR MODIFYING A FLEXIBILITY OF A BRACHYTHEREAPY CATHETER

FIELD OF THE INVENTION

This invention relates generally to methods and apparatus for use in treating proliferative tissue disorders, and more particularly to the treatment of such disorders with a multi-lumen brachytherapy device.

BACKGROUND

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it.

Radiation therapy can be administered through one of several methods, or a combination of methods, including external-beam radiation, stereotactic radiosurgery, and permanent or temporary brachytherapy. The term "brachytherapy," as used herein, refers to radiation therapy delivered by a source of therapeutic rays inserted into the body at or near a tumor or other proliferative tissue disease site.

One interstitial brachytherapy therapy system is the Mammosite® system, provided by Hologic, Inc. of Bedford, Mass. The MammoSite system includes a catheter shaft with an inflatable balloon mounted on its distal end. A lumen extends within the catheter shaft, into the balloon. The catheter shaft is inserted into a body so that the balloon is positioned within a resected cavity. The balloon is subsequently inflated and radioactive material, for example in the form of one or more radioactive seeds, is loaded into the lumen for radiation delivery.

A typical breast brachytherapy radiation treatment plan involves insertion of the balloon by a doctor during a lumpectomy. During a series of follow up visits, a radiologists delivers radiation dosing to the patient by loading radioactive material into the balloon catheter for a determined period of time to achieve a desired dosage. The brachytherapy catheter system is removed upon completion of treatment. Although the catheter must have sufficient rigidity for insertion into the resected cavity, because the brachytherapy catheter system is left in place between treatments it is desirable that the catheter be flexible; rigid catheter designs not only cause patient discomfort but may result in undesirable torque of the balloon which results in a shift of balloon location between treatments.

In single lumen brachytherapy catheters, the lumen is generally centered within the balloon such that the balloon generates isodose profiles in the target tissue that are substantially symmetrical, similar in shape to the inflated balloon. However, symmetric dosing may not always be desirable, as the resection cavity may not be uniform or regular in shape and size. Asymmetric dosing methods, such as those described in U.S. Pat. No. 6,749,555 include catheters with multiple lumens, where radioactive seeds may be placed within the different lumens to achieve different dosing profiles. Methods and systems for using multiple lumens for interstitial breast brachytherapy are also described by Lubock in U.S. Patent application publication number 20070167667, and by Cutrer in U.S. Patent application publication number 20070142694.

One problem with existing multi-lumen designs is that they increase the rigidity of the catheter, concomitantly increasing patient discomfort and the occurrence of balloon movement subsequent to initial placement. It would be desirable to identify a design for multi-lumen brachytherapy device which overcomes the problems of the prior art.

SUMMARY

According to one aspect of the invention, a stylet includes a stylet shaft having a distal end and a proximal end, a key feature at the distal end of the shaft for engaging a lock feature of a rigid structure located at a distal end of a brachytherapy device and a tab feature located at a proximal end of the shaft.

According to another aspect of the invention, an implantable apparatus for treating a proliferative disorder in a patient comprising a plurality of separate flexible dosing lumens, each having a proximal end and a distal end, wherein each distal end of each dosing lumen extends into a different one of the plurality of openings of a rigid member, the rigid member including a lock feature and a stylet comprising a key feature, the stylet for selectively modifying a rigidity of the implantable apparatus by selective engagement of the key feature with the lock feature.

According to a further aspect of the invention, a method for controlling the rigidity of a brachytherapy device that includes a plurality of flexible lumens attached at a distal end and gathered between a proximal end and a distal end by a hub, the method including the steps of inserting a rigid stylet through a hub of the brachytherapy device towards the distal end of the device, the stylet having a key feature and, the distal end of the device having a lock feature, and inserting the key feature of the device into the lock feature of the device to increase the rigidity of the device.

According to an additional aspect of the invention, a method for controlling the rigidity of a brachytherapy device that includes a plurality of flexible lumens attached at a distal end and gathered between a proximal end and a distal end by a hub, the method including the steps of removing a rigid stylet that extends through a hub of the brachytherapy device towards the distal end of the device, the stylet having a key feature and the distal end of the device having a lock feature, the key feature of the device engaging the lock feature of the device prior to the step of removing, wherein the step of removing includes the step of unlocking the key feature from the lock feature and removing the stylet to increase the flexibility of the device.

DETAILED DESCRIPTION

A flexible multi-lumen brachytherapy catheter of the present invention includes a plurality of loose lumens which are connected only at their distal ends. Reducing the binding of the lumens to a single connection permits individualized movement of the lumens, thereby decreasing the rigidity of the device and concomitantly increasing patient comfort and reducing the opportunity for shifting of the device following placement.

Figure 1:
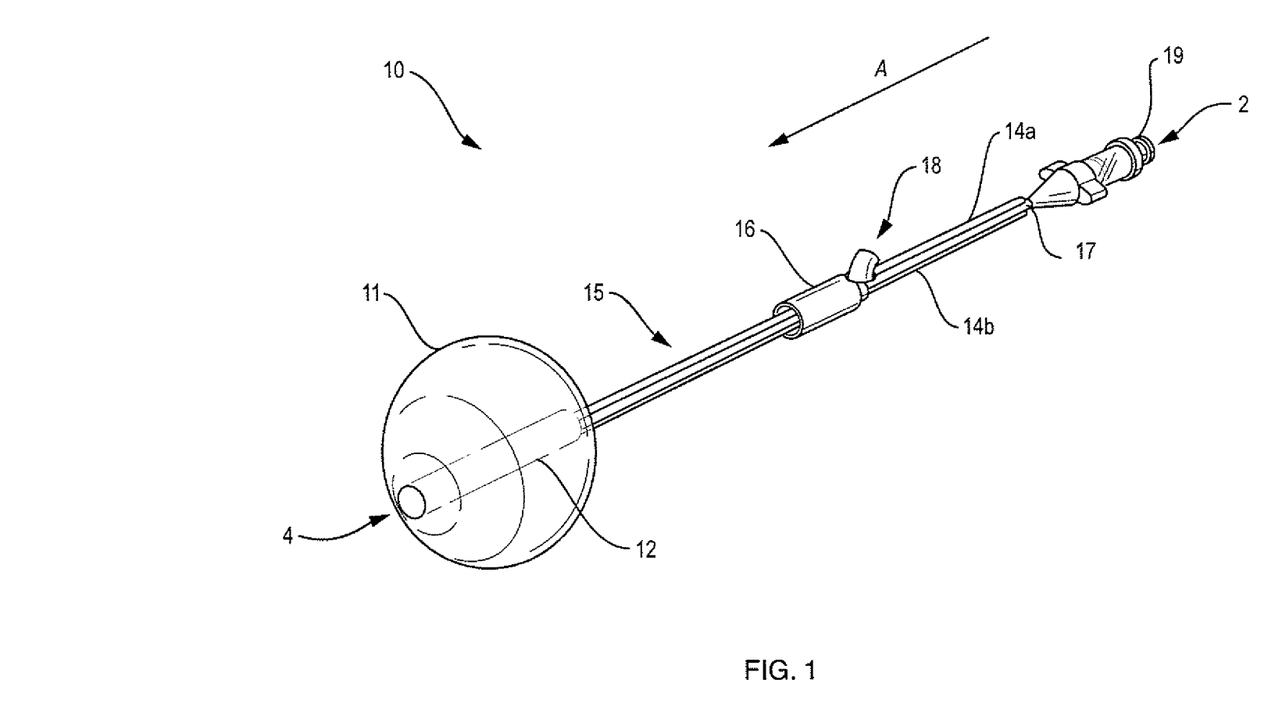
FIG. 1 is a diagram of the flexible multi-lumen brachytherapy device of the present invention.

An exemplary embodiment of a brachytherapy device 10 is shown in FIG. 1 to include a flexible shaft 15 including a proximal end 2 and a distal end 4. The flexible shaft is comprised of a plurality of flexible dosing lumens 14a and 14b and an inflation lumen 17. Each dosing lumen is sized to accommodate one or more radiation sources. Providing multiple dosing lumens facilitates customization of radio-isotope treatment profiles. It should be noted that although only two dosing lumens are visible in FIG. 1, the present invention may be implemented with any number of dosing lumens. The inflation lumen 17 is coupled at a proximal end to a connector 19. The lumens 14a, 14b and 17 are made, for example, from a flexible material such as Nylon, Pebax, LDPE, Hytrel, PEEK. Each lumen 14a, 14b, 17 slideably extends through holes in the hub 16 and into openings which extend longitudinally into the rigid section 12. The openings in the rigid section are sized so that the exterior of each lumen is tightly received in its respective opening. The lumens may be fixedly attached to the rigid section 12 using an adhesive.

An inflatable member, shown as balloon 11, envelops at least a portion of the rigid member 12. In operation, the inflatable member is inflated by coupling the device to a source of a gas or other liquid via connector 19. The inflation liquid flows into the member via the inflation lumen 17. One or more inflation holes (not shown) extend through the inflation lumen and rigid section into the inflatable member. When the inflatable member is positioned in the resected cavity, the gas or other liquid is forwarded through the inflation lumen into the inflatable member to secure the member within the cavity. Once the member is inflated, connector 19 is detached from the source.

The hub 16 collects but does not connect the lumens; in some embodiments, the portion of the flexible shaft between a distal end of the hub and a proximal end of the rigid balloon section may be sheathed in a catheter, although it is not a requirement of the invention. The hub 16 includes one or more holes extending there through, where the holes in the hub have clearance tolerances that allow the lumens to independently move axially and rotatably within the hub.

Because the multiple lumens of the device 10 are flexible and independently moveable both axially and rotationally, forces experienced at the proximal end of the device 10 do not translate into movement at the distal end of the device. Reducing the propensity for movement of the shaft also increases the comfort of the patient.

Figure 2:
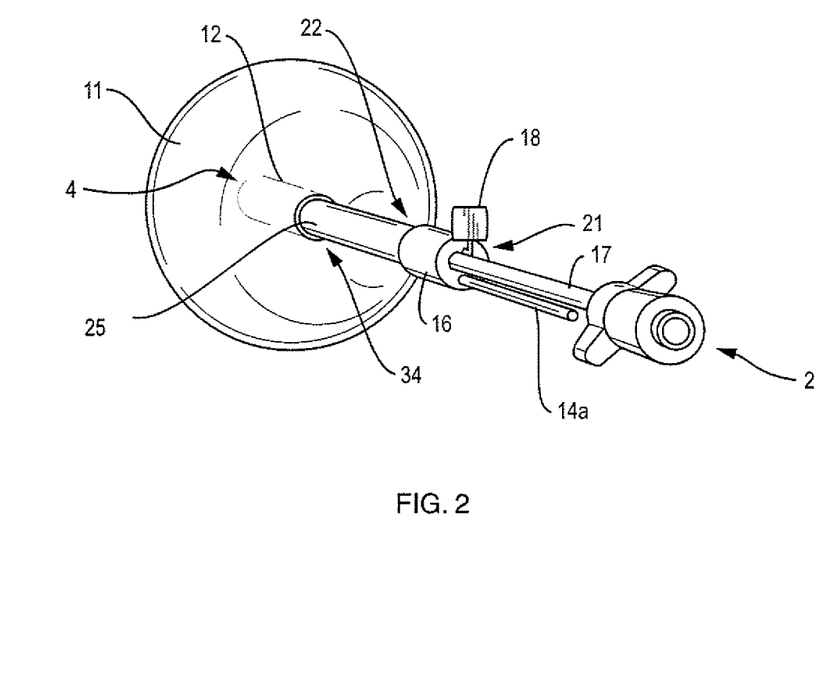
FIG. 2 is a diagram of a second embodiment of the flexible multi-lumen brachytherapy device of the present invention.

FIG. 2 is a view of the brachytherapy device taken along the perspective of line A of FIG. 1 and illustrates an embodiment of a brachytherapy device of the present invention comprising a catheter 25 disposed between the distal end of the hub and the proximal end 34 of the rigid section 12.

Figure 3A:
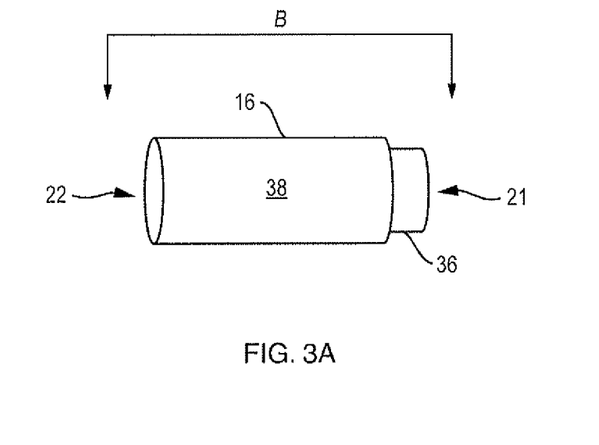
FIGS. 3A-3C include diagrams of various embodiments of a hub of the brachytherapy device of FIG. 1 or 2, the embodiments illustrated at various perspectives.

FIG. 3A is a side perspective of the hub 16. In one embodiment the hub is formed from a photosensitive resin using stereolithography. The hub 16 includes a distal end 22 and proximal end 21. In FIG. 3A, the proximal end is shown to include a collar portion 36 and a body portion 38, wherein the collar portion has a circumference which is less than the body portion. It should be noted that the hub may take many forms; in a simplest form the hub may merely be fixed circumference tube. The hub is not limited to a cylindrical shape; rather embodiments wherein the hub comprises one or more angular features are further envisioned. A principle purpose of the hub is to gather the lumens. Thus, the only limitation to the hub is that it provides sufficient space to permit free rotational and axial movement of the lumens, while being small enough to serve the purpose of gathering the lumens.

Figure 3B:
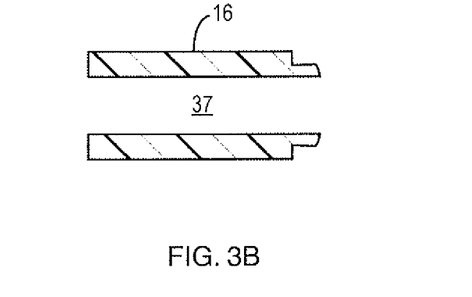
Figure 3C:
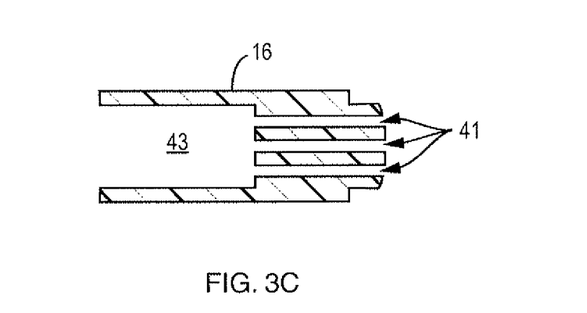

In addition, while the hub may vary in exterior shape, there are a variety of ways in which the interior passageways of the hub can be arranged. For example, FIGS. 3B and 3C illustrate cross sections of the hub taken along the plane B of FIG. 3A. In FIG. 3B, a hub 116 includes a single opening extending there through. In FIG. 3C, a hub 216 includes multiple openings 41 which extend partially through the hub into a larger opening 43. As will be described in more detail below, the hub may also include a separate hole for accommodating a keyed stylet, although it is not a requirement of the invention.

Figure 4A:
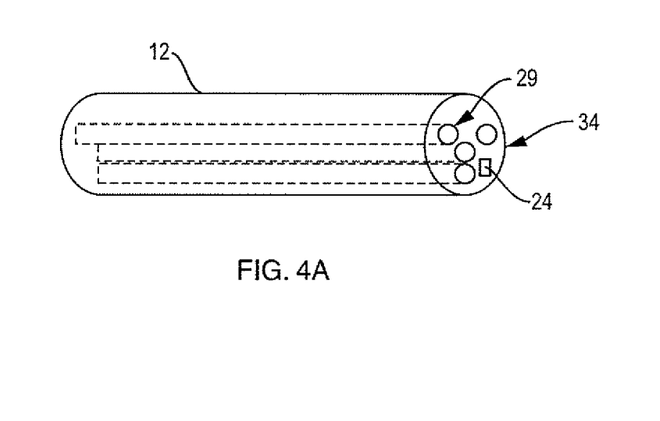
FIGS. 4A-4E are diagrams of different perspectives and different embodiments of the rigid section of the device of FIG. 1 or 2, illustrating various geometries.

FIG. 4A is a side view of the rigid section 12. The rigid section 12 includes one or more holes 22 for accepting lumens. As shown in dashed lines in FIG. 4A, the holes extend longitudinally towards the distal end 4 of the rigid section. In addition, in a preferred embodiment the rigid section 12 includes a lock or other feature 24 for engaging the keyed stylet. The rigid section 12, like the hub, may be formed from a photosensitive resin using stereolithography to define the openings.

Figure 4B:
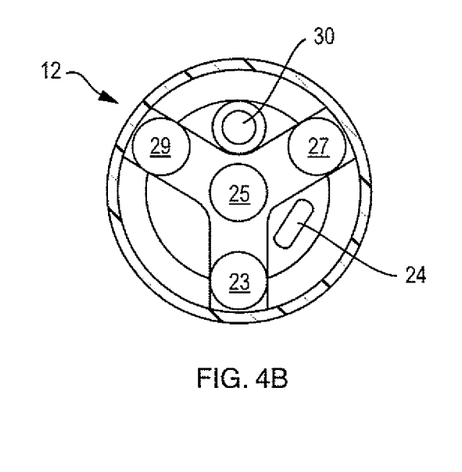

FIG. 4B is a drawing of a cross section of the proximal end 34 of one geometrical embodiment of the rigid section 12. The rigid section 12 includes an opening 23, 25, 27 and 29 for accepting each of the dosing lumens. In addition, the rigid section 12 includes an opening 30 for accepting the inflation lumen 17. Each of the dosing lumens as well as the inflation lumen extends into one of the dosing lumen openings 23, 25, 27 and 29, where they are fixedly attached to the rigid section 12. The attachment to the rigid section is the sole attachment point of each dosing lumen to the device 10. One technique for affixing the dosing lumen to the dosing lumen opening is to apply adhesive to the distal end of the dosing lumen prior to insertion of the dosing lumen into one of the openings. Other methods of securing the dosing lumens, such as through the use of heat, mechanical locks, over-molding, etc, may be readily substituted herein as equivalents.

Figure 4C:
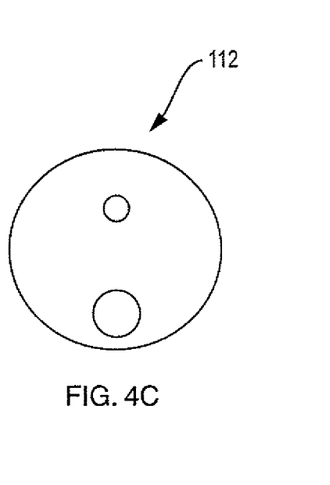
Figure 4D:
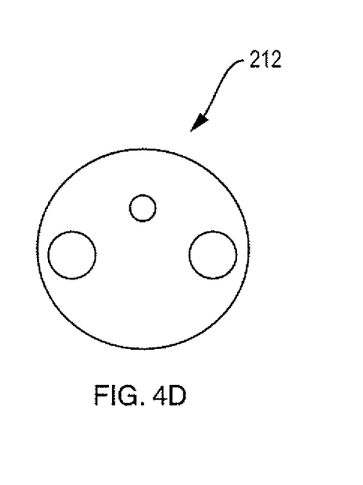
Figure 4E:
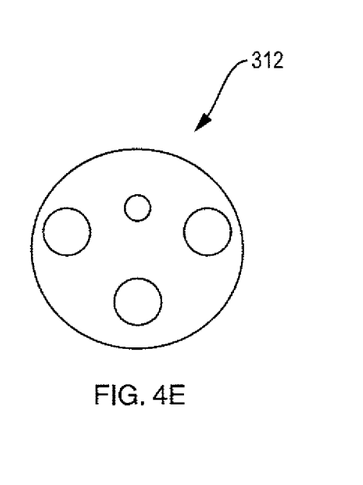

The geometry of the rigid section that is illustrated in FIG. 4B enables the use of 4 dosing lumens in a brachytherapy device, thus expanding the variety of isodose profiles which may be delivered during treatment. Radioactive material may be loaded into any or all of the dosing lumens, in different amounts and in different positions along the rigid section to satisfy a variety of dosing needs. It should be noted that FIG. 4B is merely an example of one multi-lumen dosing geometry; other geometries may be substituted by one of skill in the art herein without affecting the scope of the invention. The geometries include, but are not limited to, the use of the geometry shown in FIG. 4B with one or more of the lumen openings 29, 25, 27 or 23 removed; such geometries include the geometry of FIG. 4C to support one inflation lumen and one offset dosing lumen, the geometry of 4D which supports two offset lumen and the geometry of FIG. 4E, supporting three offset lumen. Other geometries can be substituted herein without affecting the scope of the present invention. It is further noted that although the inflation lumen 30 is shown in a particular position, there is no limitation as to the positioning of the inflation lumen so long as one or more openings are provided from the inflation lumen opening 30 into the inflatable member 11.

Figure 5A:
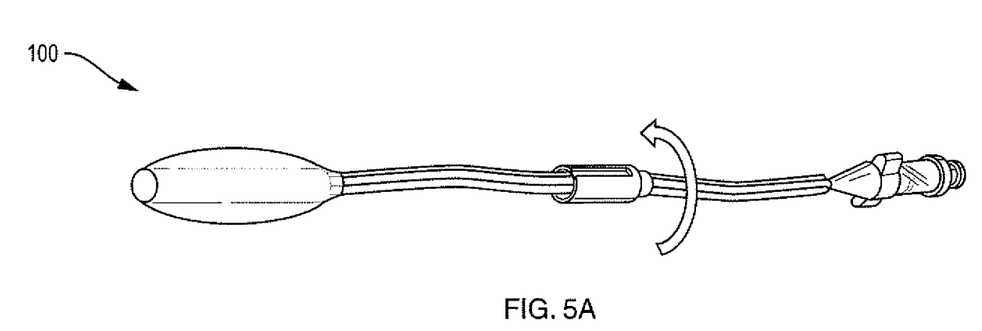
FIGS. 5A and 5B are diagrams of the device of the present invention, illustrating the flexibility of the device in the presence of torque near the proximal end of the device.
Figure 5B:
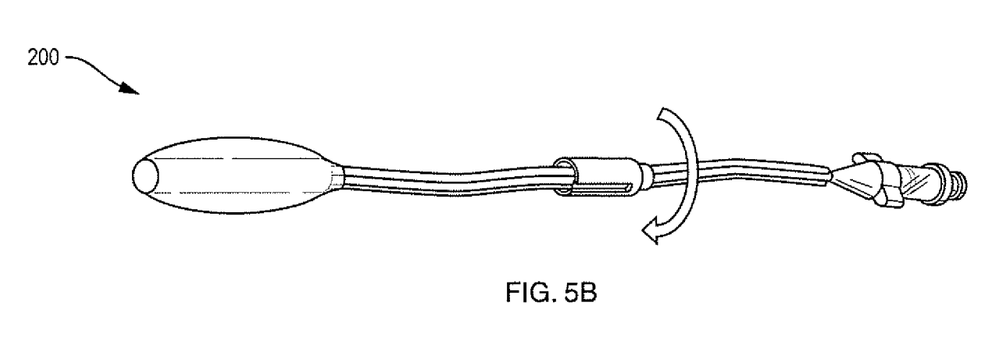

FIGS. 5A and 5B show brachytherapy devices designed according to the concepts of the present invention, having various forces applied thereto. Devices 100 and 200 are manipulated to provide a respective clockwise and counter clockwise torque upon the catheter; however, a rotation of less than ninety (90) degrees at the proximal end transmits no torque to the rigid section 12.

Accordingly, a multi-lumen brachytherapy solution with increased flexibility has been shown and described as having several advantages over the prior art. The flexibility of the multi-lumen catheter reduces the chance that external forces, acting upon the device will cause a shift in position of the device subsequent to placement. Because device placement remains stable following insertion, its location can be relied upon in temporally spaced, multi-dosing treatment plans. In addition, because the increased flexibility increases patient comfort, the likelihood that the device remain in situ during the course of treatment is increased.

Keyed Stylet Feature

While there are several advantages to the flexibility of the multi-lumen brachytherapy device of the present invention, this flexibility presents a problem when controlled insertion of the device into patient is required. Controlled placement of the device requires the device to have a certain amount of rigidity.

Figure 6A:
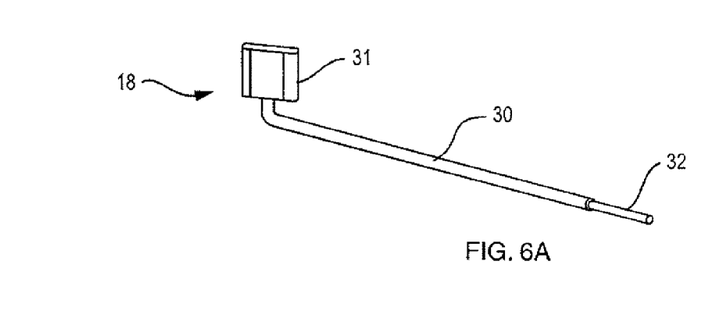
FIG. 6A illustrates a keyed stylet of the present invention, which includes a key feature at its distal end.

Accordingly, according to one aspect of the invention and referring now to FIG. 6A, rigidity of the device can be provided during placement using a keyed stylet 18. The keyed stylet 18 includes a shaft 30 with a key feature 32 on a distal end and a tab 31 on the proximal end. The key feature 32 is formed to engage the lock 24 at the proximal end of the rigid feature 12. The keyed stylet extends from the proximal end of the hub into the lock of the proximal end of the rigid section 12. Tab 31 is formed so that it extends away from the hub when the key feature engages the lock, thereby facilitating access to the tab for removal of the stylet once the device 10 is in place in the resected cavity. By keying the rigid section and connecting it with the hub 16, a one to one rotation of the device can be obtained. Although a key feature/lock combination is shown, it should be appreciated that equivalent devices for releasably mating the stylet to the rigid shaft may readily be substituted herein. For example, a distal end of the stylet may extend into any feature of the rigid section, or may be formed to hook or latch onto some feature of the rigid section. Other embodiments, where the stylet extends up to, but not into, the rigid section are also envisioned.

Figure 6B:
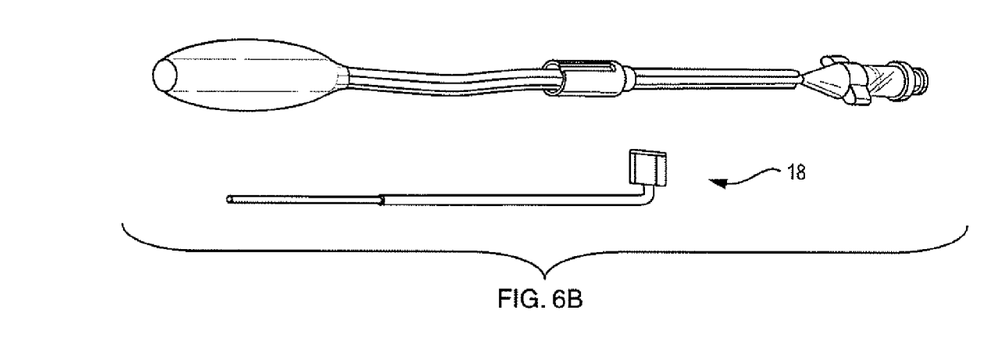
FIGS. 6B and 6C illustrate the relationship between the keyed stylet and the device, in an inserted and removed state.
Figure 6C:
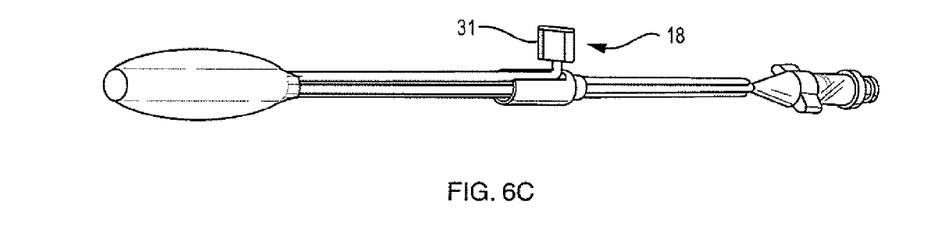

FIGS. 6B and 6C illustrate the keyed stylet and the device, prior to and following insertion of the stylet through the hub and into the rigid member. As shown in FIG. 6B, the length of the stylet is generally selected to provide control of the device during placement; the length may therefore range from a maximum length equal to the entire length of the dosing lumens to a minimum length equivalent to the depth of the resection cavity. The tab 31 is a feature which allows the surgeon to easily withdraw the stylet once the device 10 is in place. Although a tab 31 is shown, any means that provides extraction, such as a loop or the like could be readily substituted herein. In addition, other embodiments in which the stylet is latched, spring loaded or the like could be substituted herein as equivalents. In one embodiment, the stylet is formed from a stiffening material such as plastic, metal or combination, although any material that provides a rigidity sufficient to rotate the device can be readily substituted herein.

As shown in FIG. 6C, the key feature of the stylet is inserted into the proximal end of hub 16, and extends into the lock 24 at the base of the rigid section 12. In one embodiment, the hub may include a slot for accepting the tab 31. In other embodiments, the tab 31 will sit above the hub, as shown in FIG. 5. One advantage of having the tab extend over the hub is that it provides a protuberance which is associated with the geometry of the device; for example, if the surgeon is aware that the lock is 24 is positioned relative to any of the geometries of FIGS. 4A-4E, the surgeon can position the device so that the geometry best suits a radiation profile suitable for the extracted lesion. However the tab is arranged, once the stylet key feature is in the lock 24, at least a portion of the device 10 has sufficient rigidity for easy manipulation.

Figure 7:
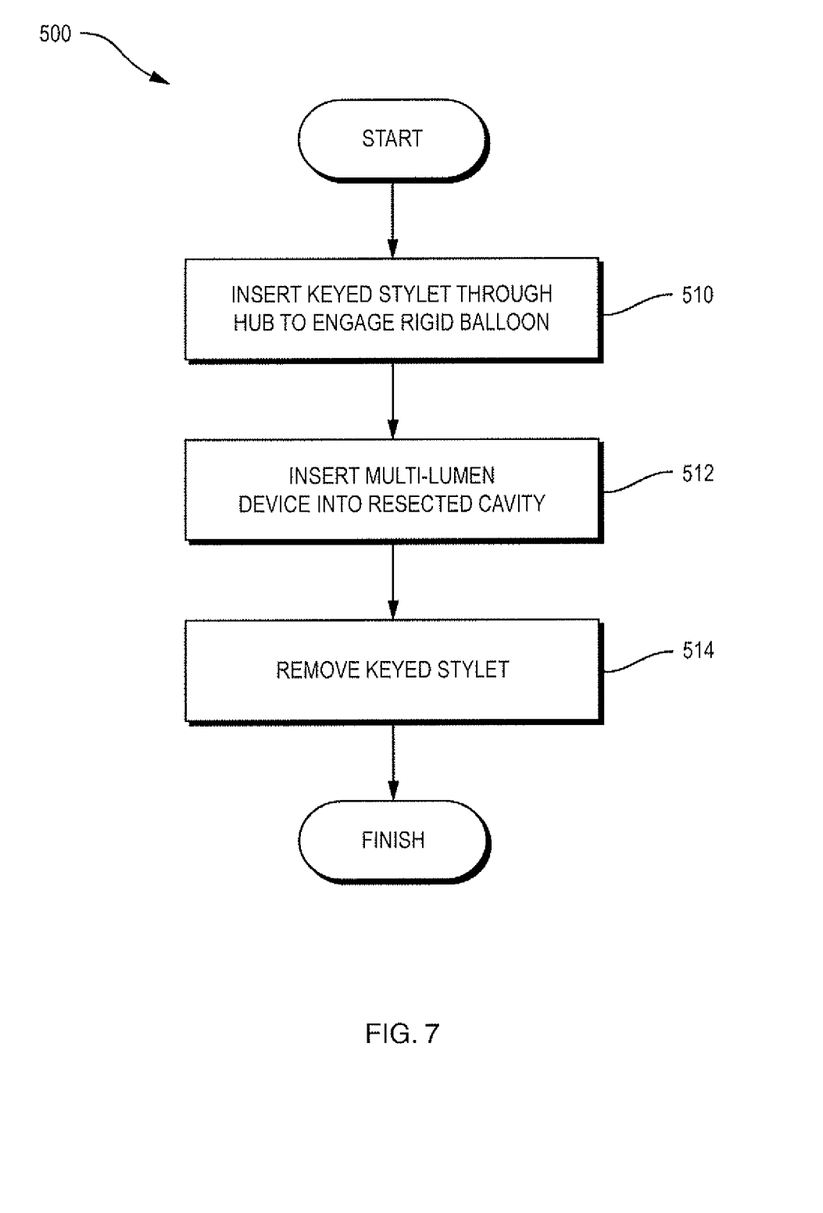
FIG. 7 is a flow diagram illustrating exemplary steps that may be performed to deploy and use the flexible brachytherapy device of the present invention in a resected cavity.

FIG. 7 is a flow diagram of an exemplary process 500 that may be performed to use the device of the present invention. At step 510 the keyed stylet is inserted through the hub such that the key feature engages the lock. As a result, the device is rigid and may be inserted into a patient. The stylet may be packaged separately from the brachytherapy device 10 and inserted by the doctor prior to insertion, or the stylet maybe inserted into the device as part of the manufacturing process. Once the stylet is introduced into the device, the device has sufficient rigidity for placement. At step 512 the device is inserted into the resected cavity, and the surgeon may rotate the device to a desired location for treatment.

At step 514, the stylet is removed. The removal of the stylet releases the rigidity of the device 10, and the resultant flexible multi-lumen brachytherapy catheter is resistant to movement caused by external forces.

In general the placement of the catheter is temporally spaced from the treatment of the patient using the catheter. Thus, once the patient is ready for treatment, the radiologist can use any of the lumens of the multi-lumen catheter to implement a treatment plan customized for the individual. Because of the flexibility of the design, the radiologist can have increased confidence in the stability of the placement of the device. However, should the radiologist need to adjust the device, he or she can easily and accurately modify the device positioning by re-inserting the key through the hub and into the device.

Accordingly, a flexible, multi-lumen brachytherapy device has been shown and described which has several advantages over the prior art. The flexibility of the design decreases intermittent device movement while increasing patient comfort. A novel keyed stylet can be selectively inserted to increase the rigidity of the device as needed. The ability to dynamically modify the rigidity of the brachytherapy device provides a comprehensive brachytherapy solution that satisfies concerns of the patient, the surgeon and the radiologists.

Having described exemplary embodiments of the invention, it should be appreciated that the present invention may be achieved using other components to perform similar tasks. For example, although an example of a keyed stylet has been shown, any rigid structure, such as a pin or rod, adapted for removable mating with the flexible catheter may be substituted herein as an equivalent. Although various exemplary embodiments of the invention have been disclosed, it should be apparent to those skilled in the art that various changes and modifications can be made that will achieve some of the advantages of the invention without departing from the true scope of the invention. These and other obvious modifications are intended to be covered by the appended claims.

The invention claimed is:

1. An apparatus for treating a proliferative disorder in a patient comprising:
   an implantable rigid member having a proximal end and a distal end, the implantable rigid member comprising a plurality of lumen openings extending longitudinally within the implantable rigid member, and wherein the proximal end of the implantable rigid member defines a lock opening;
   a plurality of separate flexible dosing lumens, each having a proximal end and a distal end, wherein each distal end of each dosing lumen extends into a different one of the plurality of lumen openings of the implantable rigid member and wherein the distal end of each dosing lumen is spaced apart from the proximal end of the implantable rigid member;
   a hub discrete from the implantable rigid member and disposed about the plurality of dosing lumens, wherein the hub defines a slot defined by an outer circumferential surface of the hub; and
   a stylet comprising a shaft having a distal end and a proximal end and a key feature at the distal end of the shaft, wherein an exterior of the shaft has a uniform shape along a length of the shaft from the proximal end of the shaft to the distal end of the shaft and wherein the key feature removably mates with the lock opening of the implantable rigid member, and wherein the proximal end removably mates with the slot defined by the hub, such that mating engagement between the stylet and both the lock opening and the slot allows for a one-to-one axial rotation of the implantable rigid member and the hub, whereby an axial rotation of the stylet causes a corresponding axial rotation of the implantable rigid member and the hub.

2. The apparatus of claim 1, wherein the stylet further comprises a tab at the proximal end and wherein the shaft extends between the key feature and the tab.

3. The apparatus of claim 1 further comprising an implantable inflatable member, the implantable inflatable member enveloping at least a portion of the rigid member.

4. The apparatus of claim 1 wherein the hub comprises a plurality of holes extending there through, wherein each of the plurality of holes is sized such that each of the plurality of dosing lumens is configured to independently move axially and rotatably within the hub.

5. The apparatus of claim 1 wherein the hub comprises a collar portion and a body portion, a circumference of the collar portion being less than a circumference of the body portion.

6. The apparatus of claim 1 wherein the stylet comprises a tab feature located at an end of the shaft.

7. The apparatus of claim 1 wherein each of the dosing lumens is fixedly attached to an interior of a respective opening of the implantable rigid member.

8. The apparatus of claim 1 wherein the stylet is rigid such that rigidity of the stylet allows the stylet to selectively modify the rigidity of the apparatus and imparts rigidity to the at least a portion of the apparatus.

9. The apparatus of claim 1, wherein the hub defines at least one hole extending therethrough, wherein the plurality of dosing lumens are disposed in the at least one hole.

10. The apparatus of claim 1, wherein the hub defines a plurality of holes extending therethrough, wherein at least one of the plurality of dosing lumens are disposed in each of the plurality of holes.

11. An apparatus for treating a proliferative disorder in a patient comprising:
   an implantable rigid member having a proximal end and a distal end, the implantable rigid member comprising a lumen opening extending longitudinally within the implantable rigid member, the implantable rigid member further comprising a lock opening defined by the proximal end;
   a dosing lumen having a proximal end and a distal end, wherein the distal end of the dosing lumen extends into the lumen opening of the implantable rigid member;
   a hub discrete from the implantable rigid member and disposed about the dosing lumen, wherein the hub defines a slot defined by an outer circumferential surface of the hub; and
   a stylet comprising a shaft having a distal end and a proximal end and a key feature at the distal end of the shaft, wherein the key feature removably mates with the implantable rigid member at the lock opening, and a portion of the proximal end mates with the slot of the hub, such that mating engagement between the stylet and both the lock opening and the slot allows for a one-to-one axial rotation of the implantable rigid member and the hub, whereby an axial rotation of the stylet causes a corresponding axial rotation of the implantable rigid member and the hub.

12. The apparatus of claim 11, wherein the stylet further comprises a tab at the proximal end and wherein the shaft extends between the key feature and the tab.

13. The apparatus of claim 12, wherein the key feature of the stylet is added for insertion in the lock opening of the implantable rigid member.

14. The apparatus of claim 11 further comprising an implantable inflatable member, the implantable inflatable member enveloping at least a portion of the implantable rigid member.

15. The apparatus of claim 11, wherein the hub comprises a hole extending there through, wherein the hole is sized such that the dosing lumen is configured to independently move axially and rotatably within the hub.

16. The apparatus of claim 11, wherein the stylet comprises a tab feature located at an end of the shaft.

17. The apparatus of claim 11, wherein the stylet is rigid such that rigidity of the stylet allows the stylet to selectively modify the rigidity of the apparatus and imparts rigidity to the at least a portion of the apparatus.

* * * * *